United States Patent
Wu et al.

(10) Patent No.: US 10,161,749 B1
(45) Date of Patent: Dec. 25, 2018

(54) OPTIMIZING WATER QUALITY SENSOR PLACEMENT FOR WATER DISTRIBUTION SYSTEMS

(71) Applicant: Bentley Systems, Incorporated, Exton, PA (US)

(72) Inventors: Zheng Yi Wu, Watertown, CT (US); Ehsan Roshani, Guelph (CA)

(73) Assignee: Bentley Systems, Incorporated, Exton, PA (US)

( * ) Notice: Subject to any disclaimer, the term of this patent is extended or adjusted under 35 U.S.C. 154(b) by 540 days.

(21) Appl. No.: 14/726,189

(22) Filed: May 29, 2015

Related U.S. Application Data (63) Continuation-in-part of application No. 14/563,668, filed on Dec. 8, 2014, now Pat. No. 9,964,468.

(51) Int. Cl.
| | |
|---|---|
| *G01B 21/16* | (2006.01) |
| *G01N 33/18* | (2006.01) |
| *G06Q 10/04* | (2012.01) |
| *G06Q 50/06* | (2012.01) |
| *G06F 17/50* | (2006.01) |
| *F17D 5/02* | (2006.01) |

(52) U.S. Cl.
CPC .............. *G01B 21/16* (2013.01); *G01N 33/18* (2013.01); *F17D 5/02* (2013.01); *G06F 17/5009* (2013.01); *G06Q 10/04* (2013.01); *G06Q 50/06* (2013.01)

(58) Field of Classification Search
CPC .......................... G06Q 10/043; G06F 17/5009
See application file for complete search history.

(56) References Cited

U.S. PATENT DOCUMENTS

| | | |
|---|---|---|
| 6,006,604 A | 12/1999 | Rabelo et al. |
| 7,574,338 B1 | 8/2009 | Kaul |
| 8,265,911 B1 | 9/2012 | Wu et al. |
| 8,301,400 B2 | 10/2012 | Beard et al. |
| 8,458,715 B1 | 6/2013 | Khosla et al. |
| 9,014,415 B2 | 4/2015 | Chen et al. |
| 9,354,043 B2 | 5/2016 | Parker et al. |
| 2002/0046144 A1 | 4/2002 | Graff |

(Continued)

OTHER PUBLICATIONS

Wu, Optimal Calibration Method for Water Distribution Water Quality Model, Journal of Environmental Science and Health Part A, 4I:I-I6, 2006.*

(Continued)

*Primary Examiner* — Michael Dalbo
(74) *Attorney, Agent, or Firm* — Cesari and McKenna, LLP; James A. Blanchette (57) ABSTRACT

In one example embodiment, an analysis application is used to optimize water quality sensor placement in a water distribution network by implementing a two-part optimization solution procedure, involving building an impact database, and determining an optimized water quality sensor location set using the impact database. The optimized sensor location set may indicate locations that maximize a length of pipes where water quality variations are detectable by at least one water quality sensor. Pipe wall reaction coefficients may be used as calibration parameters, with water quality indicated to be detectable at a possible sensor location when a change in its pipe wall reaction coefficients leads to a change in water quality at the possible sensor location that is greater than a threshold.

15 Claims, 10 Drawing Sheets

(56) References Cited

U.S. PATENT DOCUMENTS

| | | | |
|---|---|---|---|
| 2005/0072234 A1 | 4/2005 | Zhu et al. | |
| 2008/0178663 A1* | 7/2008 | Yang | G01N 1/10 73/61.41 |
| 2008/0255777 A1 | 10/2008 | Beard et al. | |
| 2009/0326834 A1 | 12/2009 | Sundaresan et al. | |
| 2011/0046929 A1 | 2/2011 | Bryant | |
| 2012/0123981 A1 | 5/2012 | Graves et al. | |
| 2013/0018525 A1 | 1/2013 | Jang et al. | |
| 2013/0220902 A1* | 8/2013 | Lee, II | G05B 11/42 210/96.1 |
| 2013/0262068 A1* | 10/2013 | Israeli | F17D 5/02 703/9 |
| 2013/0327148 A1 | 12/2013 | Yan et al. | |
| 2014/0058709 A1 | 2/2014 | Viana et al. | |
| 2014/0163916 A1* | 6/2014 | Ba | G06Q 10/04 702/100 |
| 2015/0088372 A1 | 3/2015 | Nower et al. | |

OTHER PUBLICATIONS

Preis, Multi-objective Sensor Network Placement Model for Integrated Monitoring of Hydraulic and Water Quality Parameters, orld City Water Forum, WCWF, 2009.*

Walski, Multi Objective Optimization of Sensor Placement in Water Distribution Systems, 2006 Annual Symposium on Water Distribution Systems Analysis, Cincinnati, Ohio, U.S.A.*

Walski, Thomas M., Sharp, Wayne W., and Shields, F. Douglas, Jr. "Predicting Internal Roughness in Water Mains," Miscellaneous Paper EL-88-2, US Army Engineer Waterways Experiment Station, Vicksburg, Miss, 1988.*

Kumar et al., "Parameter Estimation in Water Distribution Networks", Water Resour Manage (2010) 24:1251-1272 DOI 10.1007/s11269-009-9495-1.*

Basseville, Michele et al., "Optimal Sensor Location for Detecting Changes in Dynamical Behavior", IEEE Transactions on Automatic Control, vol. AC-32, No. 12, Dec. 1987, 9 pages.

Berry, J., Fleischer, L., Hart, W. E., Phillips, C. A. and Watson, J.-P., "Sensor placement in municipal water networks" ASCE Journal of Water Planning and Resources Management, 131:237-243, Jan. 2005, pp. 1-10.

Grayman, W., Speight, V., and Uber, J., "Using Monte-Carlo Simulation to Evaluate Alternative Water Quality Sampling Plans." Water Distribution Systems Analysis Symposium, Aug. 2006, pp. 1-11.

Isovitsch, S. L., VanBriesen, J. M., "Sensor Placement and Optimization Criteria Dependencie in a Water Distribution System," J. Water Resour. Plann. Manage. vol. 134(2), Mar. 2008, pp. 186-196.

Janke, R., "Threat Ensemble Vulnerability Assessment Sensor Placement Optimization Tool (TEVA-SPOT) Graphical User Interface User's Manual," U.S. EPA National Homeland Security Research Center (NHSRC), Sep. 2012, pp. 1-109.

Krause, A., Leskovec, J., Isovitsch, S., Xu, J., Guestrin, c., VanBriesen, J., Small, M., Fischbeck, P., "Optimizing Sensor Placements in Water Distribution Systems Using Submodular Function Maximization" 8th Annual Water Distribution Systems Analysis Symposium, Cincinnati, Ohio, USA Aug. 27-30, 2006, pp. 1-17.

Papadimitriou, Costas et al., "Entropy-based Optimal Sensor Location for Structural Model Updating", Journal of Vibration and Control, vol. 6, Dec. 17, 1999, 20 pages.

Papadimitriou, C., "Optimal Sensor Placement Methodology for Parametric Identification of Structural Systems", Journal of Sound and Vibration 278, Oct. 21, 2003, pp. 923-947.

Shen, R. and McBean, E., "Pareto Optimality for Sensor Placements in a Water Distribution System." J. Water Resour. Plann. Manage. 137(3), May 2011, pp. 243-248.

Spanache, Stefan et al., "Sensor Placement Optimisation Using Genetic Algorithms", In 15th International Workshop on Principles of Diagnosis (DX'04), Jun. 23, 2004, pp. 179-184.

Speight, V., Kalsbeek, W., and DiGiano, F., "Randomized Stratified Sampling Methodology for Water Quality in Distribution Systems." ASCE J. Water Resour. Plann. Manage. 130(4), Jul. 2004, pp. 330-338.

"STAAD.Pro Technical Reference Manual", Bentley Systems Incorporated, Nov. 19, 2012, 775 pages.

U.S. Appl. No. 14/563,668, filed Dec. 8, 2014 by Zheng Yi Wu, et al. for a Optimizing Sensor Placement for Structural Health Monitoring, pp. 1-34.

Worden, K. et al., "Optimal Sensor Placement for Fault Detection", Engineering Structures 23 (2001), Nov. 16, 2000, pp. 885-901.

Wu, Z. Y., Wang, Q, Butala, S., Mi T. and Song Y., "Darwin Optimization Framework User Manual," Bentley Systems, Incorporated, Watertown, CT 06795, USA, Sep. 2012, pp. 1-40.

Wu, Z.Y. and Walski, T. M., (2006) "Multi Objective Optimization of Sensor Placement." The 8th Annual Water Distribution Systems Analysis Symposium, Cincinnati, Ohio, USA, Aug. 27-30, 2006, pp. 1-11.

Wu, Z. Y., "Optimal Calibration Method for Water Distribution Water Quality Model," Journal of Environmental Science and Health Part A, vol. 41, No. 7, Apr. 2006, pp. 1363-1378.

Wu, Zheng Yi, "Optimizing Pressure Logger Placement for Leakage Detection and Model Calibration", 14$^{th}$ Water Distribution Systems Analysis Conference, Sep. 24, 2012, 13 pages.

Yao, Leehter et al., "Sensor Placement for On-Orbit Modal Identification via a Genetic Algorithm", AIAA Journal, vol. 31, No. 10, Oct. 1993, 7 pages.

Yi, Ting-Hua et al., "Methodology Developments in Sensor Placement for Health Monitoring of Civil Infrastructures", Hindawi Publishing Corporation, International Journal of Distributed Sensor Networks, vol. 2012, Article ID 612726, Aug. 7, 2012, 12 pages.

Yi, Ting-Hua et al., "Optimal Sensor Placement for Health Monitoring if High-Rise Structure Based on Genetic Algorithm", Hindawi Publishing Corporation, Mathematical Problems in Engineering, vol. 11, Article ID 395101, Mar. 2, 2011, 13 pages.

Cobb, Richard G, & Liebst, Brad S., "Sensor Placement and Structural Damage Identification From Minimal Sensor Information," AIAA Journal, Feb. 1997, 35(2), pp. 369-374.

Gawronski, W., "Actuator and Sensor Placement for Structural Testing and Control," Academic Press Limited, Journal of Sound and Vibration, Jul. 1997, 208(1), pp. 101-109.

Glaser, S. D., Li, H., Wang, M. L., Ou, L, & Lynch, J. P., "Sensor Technology Innovation for the Advancement of Structural Health Monitoring: A Strategic Program of US-China Research for the Next Decade," Smart Structures and Systems, Jan. 2007, 3(2), pp. 221-244.

Guratzsch, Robert F., et al., "Structural Health Monitoring Sensor Placement Optimization Under Uncertainty", AIAA Journal, vol. 48, No. 7, Jul. 2010, pp. 1281-1289.

Hamdan, A.M.A., & Nayfeh, A.H., "Measures of Modal Controllability and Observability for First-and Second-Order Linear Systems," Journal of Guidance, Control, and Dynamics, May-Jun. 1989, 12(3), pp. 421-428.

Kammer, Daniel C., "Sensor Placement for On-Orbit Modal identification and Correlation of Large Space Structures," Journal of Guidance, Control, and Dynamics, Mar.-Apr. 1991, 14(2), pp. 251-259.

Kammer, Daniel C., "Sensor Set Expansion for Modal Vibration Testing," Mechanical Systems and Signal Processing, Jul. 2005, 19(4), pp. 700-713.

Kirkegaard, Poul Henning, & Brincker, Rune, "On the Optimal Location of Sensors for Parametric Identification of Linear Structural Systems," Academic Press Limited, Mechanical Systems and Signal Processing, Nov. 1994, 8(6), pp. 639-647.

Mackiewicz, Andrzej, Holnlcki-Szulc, Jan, & Lopez-Almansa, Francisco, "Optimal Sensor Location in Active Control of Flexible Structures," AIAA Journal, Mar. 1996, 34(4), pp. 857-859.

Mahfoud, Samir W, & Goldberg, David E., "Parallel Recombinative Simulated Annealing: A Genetic Algorithm," Parallel Computing, Jan. 1995, 21(1), pp. 1-28.

(56) References Cited

OTHER PUBLICATIONS

Papadimitriou, Costas, & Lombaert, Geert, "The Effect of Prediction Error Correlation on Optimal Sensor Placement in Structural Dynamics," Elsevier Ltd, Mechanical Systems and Signal Processing, 2012, vol. 28, pp. 105-127.

Shi, Z. Y., et al., "Optimum Sensor Placement for Structural Damage Detection," Journal of Engineering Mechanics, Nov. 2000, 126(11), pp. 1173-1179.

Shih, Y-T, Lee, AC, & Chen, J-H, "Sensor and Actuator Placement for Modal Identification," Academic Press, Mechanical Systems and Signal Processing, Mar. 1998, 12(5), pp. 641-659.

Udwadia, Firdaus E., "Methodology for Optimum Sensor Locations for Parameter Identification in Dynamic Systems," ASCE, Journal of Engineering Mechanics, Feb. 1994, 120(2), pp. 368-390.

* cited by examiner

| Monte Carlo Parameters | Generated Scenarios | |
|---|---|---|
| No. | Completed | Detectable | Pipe 1 |
| 1 | True | True | LINK-72 |
| 2 | True | True | LINK-148 |
| 3 | True | True | LINK-33 |
| 4 | True | True | LINK-14 |
| 5 | True | True | LINK-39 |
| 6 | True | True | LINK-15 |
| 7 | True | True | LINK-34 |
| 8 | True | True | LINK-56 |
| 9 | True | True | LINK-167 |
| 10 | True | True | LINK-85 |
| 11 | True | True | LINK-121 |

Optimization
Number of Logger: 1    Start Optimization

Back    Next    Exit

OPTIMIZING WATER QUALITY SENSOR PLACEMENT FOR WATER DISTRIBUTION SYSTEMS

RELATED APPLICATIONS

The present application is a continuation-in-part of U.S. patent Ser. No. 14/563,668 filed on Dec. 8, 2014 by Zheng Yi Wu et al., for a "Optimizing Sensor Placement for Structural Health Monitoring", the contents of which are incorporated by reference herein in their entirety.

BACKGROUND

Technical Field

The present application relates generally to sensor placement for fluid distribution systems, and more specifically to techniques for optimizing water quality sensor placement for a water distribution system.

Background Information

The quality of drinking water supplied to consumers from a water treatment plant is dependent upon many factors. These factors may include the quality of the raw (un-treated) water, the processes and chemical additives the water is treated with, and the interaction of the treated water with various water distribution system components which alters its quality (e.g., cause the chemical additives to lose their effectiveness). The quality of raw water and the treatment at the plant is generally closely monitored, such that treated water leaving a water treatment plant generally meets Environmental Protection Agency (EPA)'s water quality requirements. However, interaction with water distribution system components may impact the quality of the water, such that it is rendered unsuitable for human consumption by the time it actually reaches the end user.

To detect potential water quality problems of this type, water quality sensor networks may be deployed. A typical water quality sensor network includes a number of water quality sensors that monitor, among other things, the concentration of chemical additives at various locations (e.g., junctions) in the water distribution system, during day-to-day operation of the system. Due to budgetary constraints, generally only a limited number of water quality sensors can be deployed. To maximize the utility of the limited number of water quality sensors, it is desirable to select near optimal locations for them. However, traditionally there has not been an effective technique for determining such near optimal locations, in the context of monitoring day-to-day operation. As such, locations for water quality sensors have often been selected in an ad-hoc manner, based upon assumptions and "rules-of-thumb" concerning geographic coverage, pipe diameter, pipe material, distance to the source, accessibility, and other factors. The resulting locations are often far from optimal.

Some techniques have been developed to aid in sensor placement in the context of water security. For example, due to heightened security concerns following the Sep. 11, 2001 attacks, techniques have been developed that may aid in placing sensors to catch chemical and/or biological intrusion into water distributions systems. However, the issues faced in the context of water security are generally very different than those faced when trying to monitor water quality provided during day-to-day operation of a water distribution system. Accordingly, the prior techniques are often of limited use in the latter context. There is an outstanding need for techniques that can be used to determine near optimal locations for water quality sensors to monitor water quality during day-to-day operation of water distribution systems.

SUMMARY

In an example embodiment, an analysis application is used to optimize water quality sensor placement in a water distribution system by implementing a two-part solution procedure. The two-part solution procedure may involve 1) building an impact database, and 2) optimizing placement of a number of water quality sensors using the impact database. The result may be an optimized sensor location set that indicates locations (e.g., junctions) that maximize a length of pipes where water quality variations are detectable by at least one water quality sensor. Pipe wall reaction coefficients may be used as calibration parameters, with water quality indicated to be detectable at a possible sensor location when a change in pipe wall reaction coefficients leads to a change in water quality at the possible sensor location that is greater than a threshold.

More specifically, in an example embodiment, the analysis application may build the impact database by generating a plurality of target scenarios via a Monte Carlo simulation algorithm, and by analyzing each target scenario to determine whether water quality variation is detectable at each of a plurality of possible sensor locations The analysis of each target scenario may involve simulating the target scenario, comparing water quality (e.g., the concentration of one or more chemical additives) at each the plurality of possible sensor locations with water quality at the respective possible sensor location in a base scenario, and determining water quality is detectable when a difference in water quality is greater than a threshold value (e.g., accuracy of the water quality sensor). The results of the determination may be formatted as a binary matrix, where each binary value indicates whether water quality variation is detectable at a corresponding possible sensor location in a corresponding target scenario. The binary matrix may be stored in an impact database.

The analysis application may employ one or more additional modules to optimize placement of a number of water quality sensors at the possible sensor locations by generating a candidate water quality sensor location set, calculating water quality sensor network efficiency for the candidate water quality sensor location set using the impact database, and applying a genetic algorithm that uses the water quality sensor network efficiency as a fitness value to generate subsequent water quality sensor location sets that have greater water quality sensor efficiency. Water quality sensor network efficiency may be based on the length of pipes where water quality variations are detectable by at least one water quality sensor. The water quality sensor location sets may be evolved until a stopping criteria is satisfied, and this result returned as the optimized sensor location set. The optimized sensor location set may be displayed to a user, who may then arrange for workers to apply water quality sensors at the locations indicated.

It should be understood that a variety of additional features and alternative embodiments may be implemented other than those discussed in this Summary. This Summary is intended simply as a brief introduction to the reader for the further description that follows, and does not indicate or imply that the examples mentioned herein cover all aspects of the disclosure, or are necessary or essential aspects of the disclosure.

BRIEF DESCRIPTION OF THE DRAWINGS

The description below refers to the accompanying drawings of example embodiments, of which.

DETAILED DESCRIPTION

Figure 1:
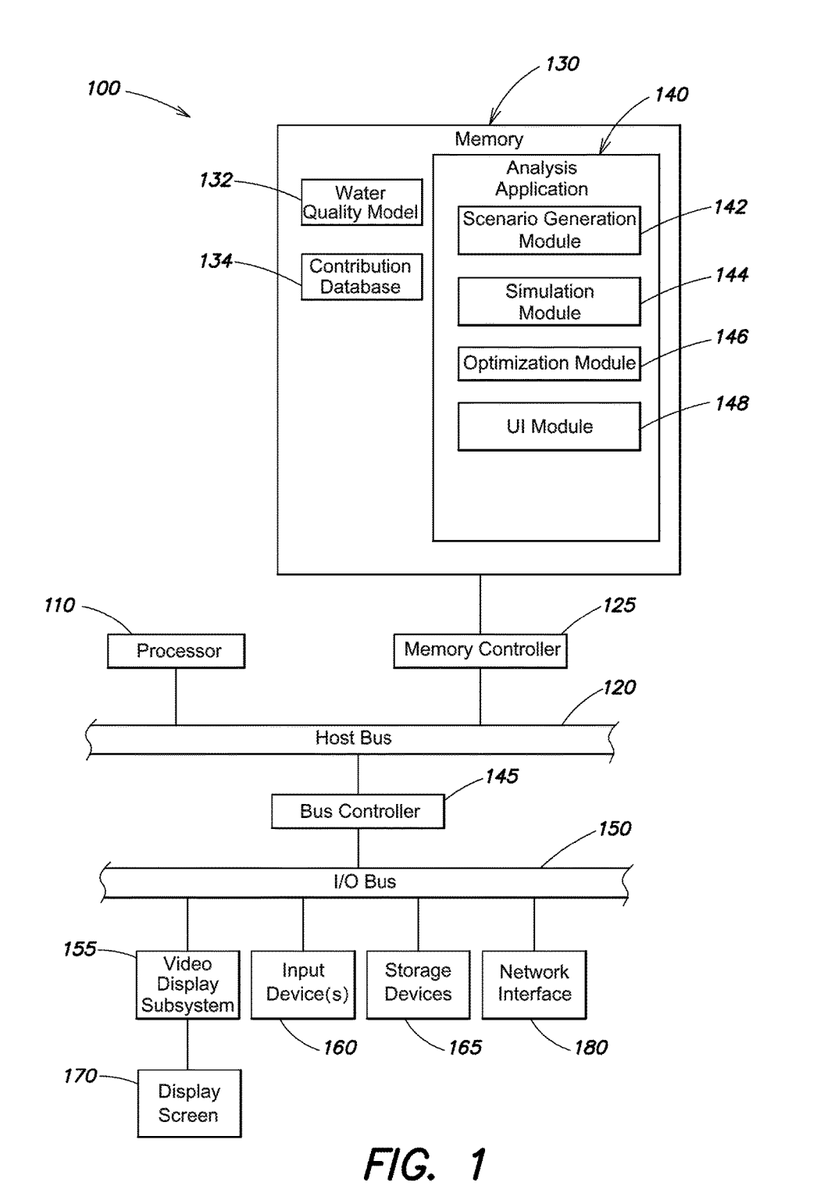
FIG. 1 is a block diagram of an example electronic device (e.g., a computer) that may be used with the present techniques.

FIG. 1 is a block diagram of an example electronic device 100 (e.g., a computer) that may be used with the present techniques. The electronic device 100 includes at least one processor 110 coupled to a host bus 120. The processor 110 may be any of a variety of commercially available processors, such as an Intel x86 processor, or another type of processor. A volatile memory 130, such as a Random Access Memory (RAM) is also coupled to the host bus 120 via a memory controller 125. When in operation, the memory 120 stores processor-executable instructions and data that are provided to the processor 110. An input/output (I/O) bus 150 is accessible to the host bust 120 via a bus controller 145. A variety of additional components are coupled to the I/O bus 150. For example, a video display subsystem 155 is coupled to the I/O bus 150. The video display subsystem may include a display screen 170 and hardware to drive the display screen. At least one input device 160, such as a keyboard, a touch sensor, a touchpad, a mouse, etc., is also coupled to the I/O bus 150. A persistent storage device 165, such as a hard disk drive, a solid-state drive, or another type of persistent data store, is further attached, and may persistently store processor-executable instructions and data, that are loaded into the volatile memory 130 when needed. Still further, a network interface 180 is coupled to the I/O bus 150. The network interface enables communication over a computer network, such as the Internet, between the electronic device 100 and other electronic devices, using any of a number of well-known networking protocols. Such communication may enable collaborative, distributed, or remote computing with functionality spread across multiple electronic devices.

Working together, the components of the electronic device 100 (and other electronic devices in the case of collaborative, distributed, or remote computing) may execute instructions for an analysis application 140 that may determine, for a user-provided number of water quality sensors, optimized locations for monitoring water quality (e.g., the concentration of one or more chemical additives, such as chlorine) during day-to-day operation of a water distribution system. The analysis application 140 may be structured as a single piece of software, or as a collection of software modules which may exchange data and otherwise interoperate.

The analysis application 140 may utilize data including a water quality model 132 of the water distribution system and an impact database 134. The water quality model 132 may represent the water distribution system in terms of pipes that are interconnected at junctions. The pipes may be identified by pipe indexes. The impact database 134 may store a binary matrix which indicates, for each a plurality of target scenarios, whether water quality is detectable at various possible sensor locations.

The analysis software package 140 may include a number of modules, such as a scenario generation module 142, a simulation module 144, an optimization module 146, and a user interface (UI) module 148. As discussed in more detail below, the scenario generation module 142 may utilize a Monte Carlo simulation algorithm to generate target scenarios used to produce the impact database 134. The simulation module 144 may include functions for performing simulation runs for the target scenarios. In one embodiment, the simulation module 144 may be the WaterCAD® water distribution is modeling and management solution available from Bentley Systems, Inc. of Exton, Pa. The optimization module 146 may employ a genetic algorithm to determine candidate sensor location sets, and evolve those candidate sensor location sets based on network efficiency, until an optimized sensor location set is determined. In one implementation, the optimization module 144 may be a generic optimization framework, such as the Darwin Optimization Framework available from Bentley Systems Inc. of Exton Pa. The UI module 148 may display a graphical UI on the display screen 170, in which a user may select the number of water quality sensor and view optimized water quality sensor locations, among other functions.

The analysis application 140, and its modules 142-148, may operate to solve a defined water quality sensor placement optimization problem. Such optimization problem may involve calibration of the water quality model 132 with pipe wall reaction coefficients (noted a $Kw_i$ for a pipe i, i=1, . . . np, were np is the number of pipes in the model). The optimization problem may be formulated to search for water quality sensor locations that maximize the length of pipes in the water distribution system where water quality variations (e.g., variations in the concentration of one or more chemical additives, such as chlorine) are detectable by at least one water quality sensor.

The efficiency of a given sensor at a potential location may be defined based on the length of pipes where variation in wall reaction coefficients can be detected, given as:

$$S_\eta = \left(\sum_{i=1}^{i=np} DL_i\right) / TPL \qquad (1)$$

where $S_\eta$ is the water quality sensor efficiency which varies from 0 (no pipe is detectable) to 1 (all the pipes are detectable), i is the pipe index, np is the number of pipes in the system, TPL is the total length of pipes in the system, and $DL_1$ is the length of the $i^{th}$ pipe that is detectable. Water quality in a pipe may be considered detectable by the given water quality sensor if a variation in pipe wall reaction coefficient leads to a variation in water quality at the potential location of the sensor that is greater than or equal to a threshold (e.g., the accuracy of the given water quality sensor).

To determine whether a variation in pipe wall reaction coefficients leads to a variation in water quality at the potential location, initial pipe wall reaction coefficients is may be determined, and an initial water quality ascertained. The initial pipe wall reaction coefficients may be set based on user experience and/or table values. The set of initial pipe wall reaction coefficients, and the initial water quality ascertained therefrom, may be refereed to herein a "base scenario." Then, new pipe wall reaction coefficients may be determined, and new water quality ascertained. The new pipe wall reaction coefficients may be determined by randomly selecting pipe indexes identifying pipes, and randomly selecting pipe wall reaction coefficients within a valid range for those pipes. The new pipe wall reaction coefficients, and the new water quality ascertained therefrom, may be refereed to herein a "target scenario." If the difference in water quality at the potential location for the base scenario and water quality at the potential location for the target scenario is greater than or equal to a threshold (e.g., the accuracy of the given water quality sensor), then the change in pipe wall reaction coefficient may be considered detectable for the target scenario. A number of target scenarios may be generated by repeatedly randomly selecting pipe indexes and pipe wall reaction coefficients.

The techniques may be extended to apply to a plurality of water quality sensors, instead of only a single sensor. Equation (1) may be expanded for the plurality of water quality sensors, as:

$$S_\eta = \left( \sum_{j=1}^{j=ns} \sum_{i=1}^{i=np} DL_i \right) / TPL \quad (2)$$

where ns is the number of water quality sensors, and j is the sensor index. Equation (2) may ensure that each pipe is only accounted for once in the water distribution system, thereby preventing from being greater than 1, and guiding the optimization to search for a more even distribution of sensor locations. $DL_i$ may be calculated as:

$$DL_i = \begin{cases} \text{if (Detectable}(P_i)\text{and Unique }(P_i)) \xrightarrow{yields} PL_i \\ \text{else} \xrightarrow{yields} 0 \end{cases}$$

where $P_i$ is the $i^{th}$ pipe, Detectable( ) is a function that evaluates the pipe to see if it is detectable, and Unique( ) is a function that checks to see whether the pipe has been accounted for before or not, and $PL_i$ is the length of pipe i. To ease in optimization, Equation (2) may be reformulated for minimization. When so reformulated, instead of accounting for detectable pipes, undetectable pipes may be accounted for.

Figure 2:
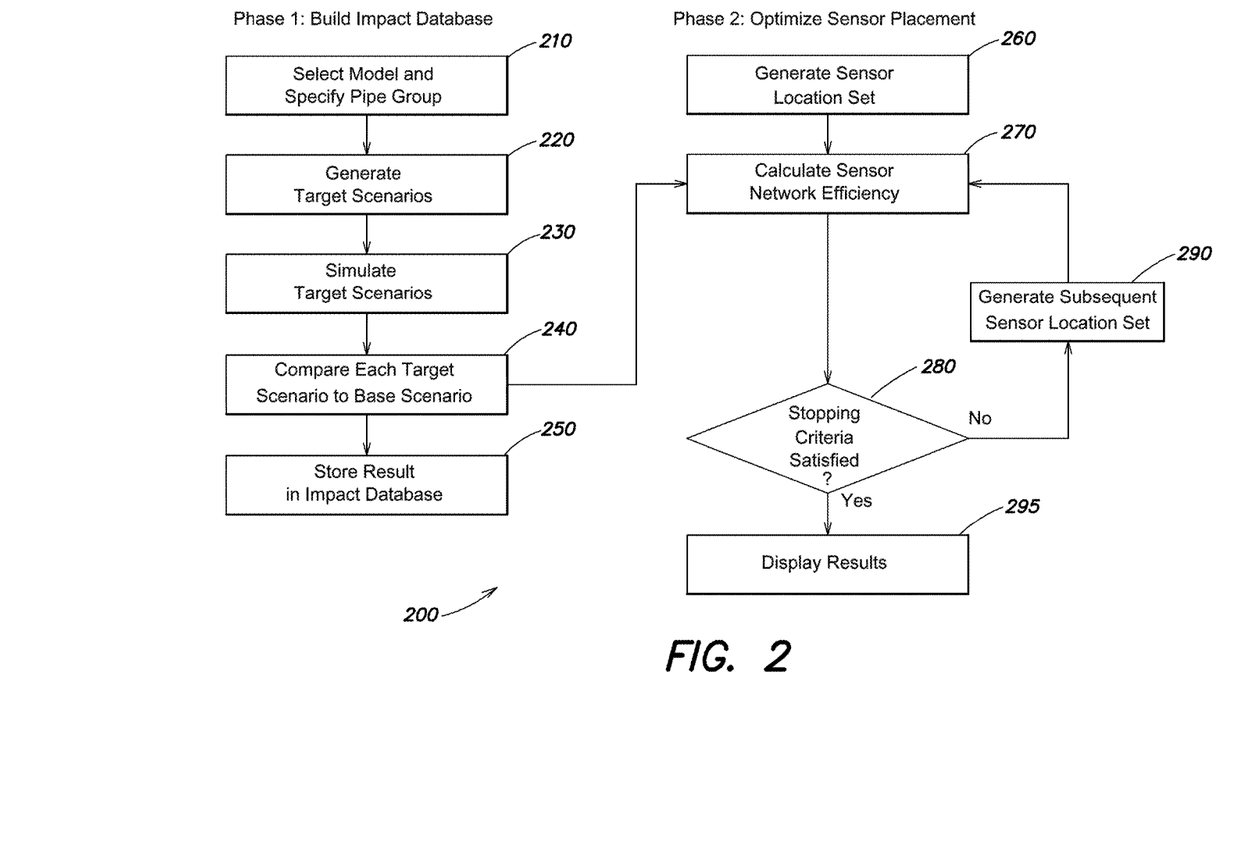
FIG. 2 is a flow diagram of a sequence of steps that may be implemented for optimizing water quality sensor placement.
Figure 3A:
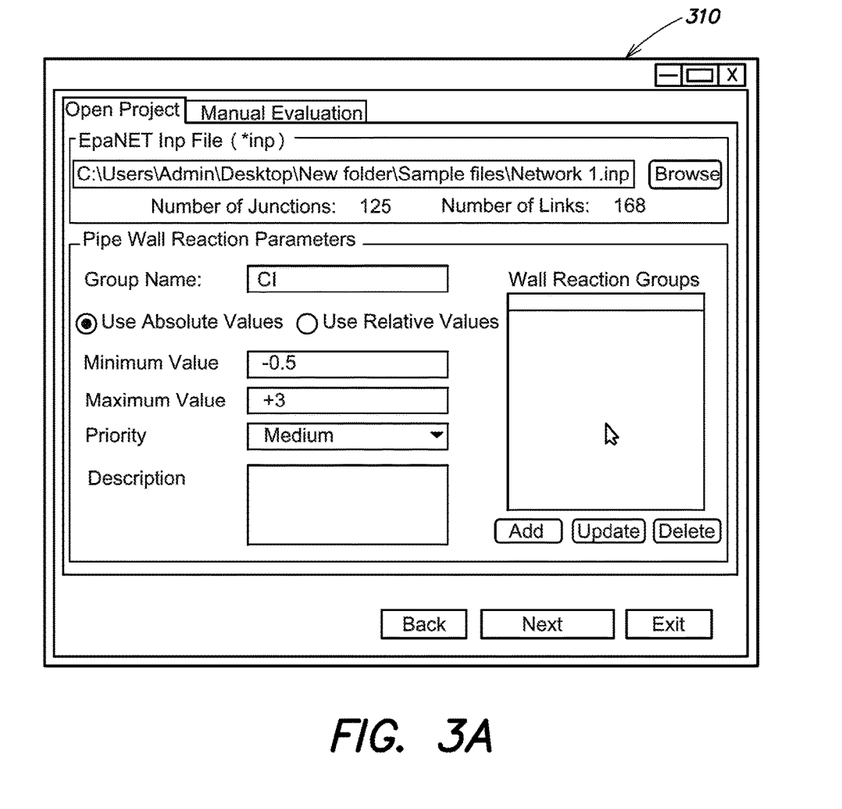
FIG. 3A is a screen shot of an example model selection and group creation UI screen.

The analysis application 140, and its modules 142-148, may operate to solve the is water quality sensor placement optimization problem in two phases: (1) build the impact database and (2) optimizing placement of a number of water quality sensors using the impact database. FIG. 2 is a flow diagram of a sequence of steps 200 that may be implemented for optimizing water quality sensor placement. Beginning with the building of the impact database phase, at step 210, the water quality model 132 may be selected and pipe groups specified, including valid ranges for their pipe wall reaction coefficients. Due to the large number of pipes included in typical water quality models, pipes with the same or similar characteristics (e.g., diameters, material and pipe age within the same neighborhood or on the same flow path, etc.) may be aggregated into one group that has a same pipe wall reaction coefficient. The UI module 148 may present to a model selection and group creation UI screen that allows a user to make perform such tasks. FIG. 3A is a screen shot of an example model selection and group creation UI screen 310.

Figure 3B:
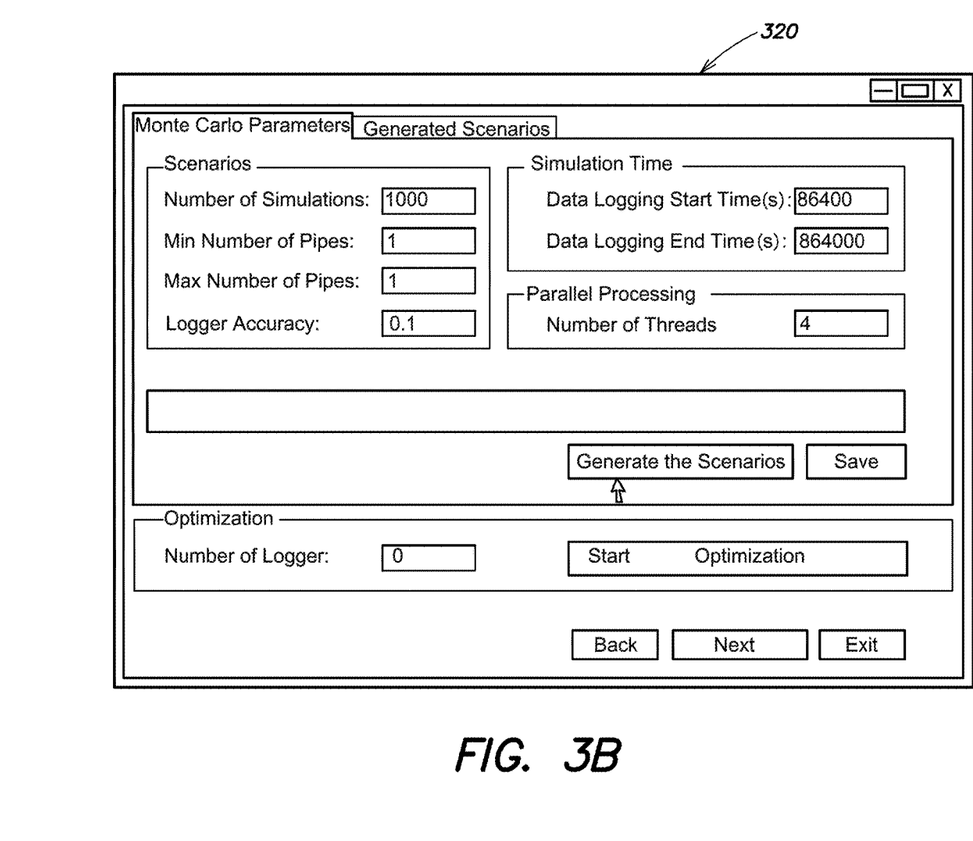
FIG. 3B is a screen shot of an example scenario generation UI screen.
Figure 3C:
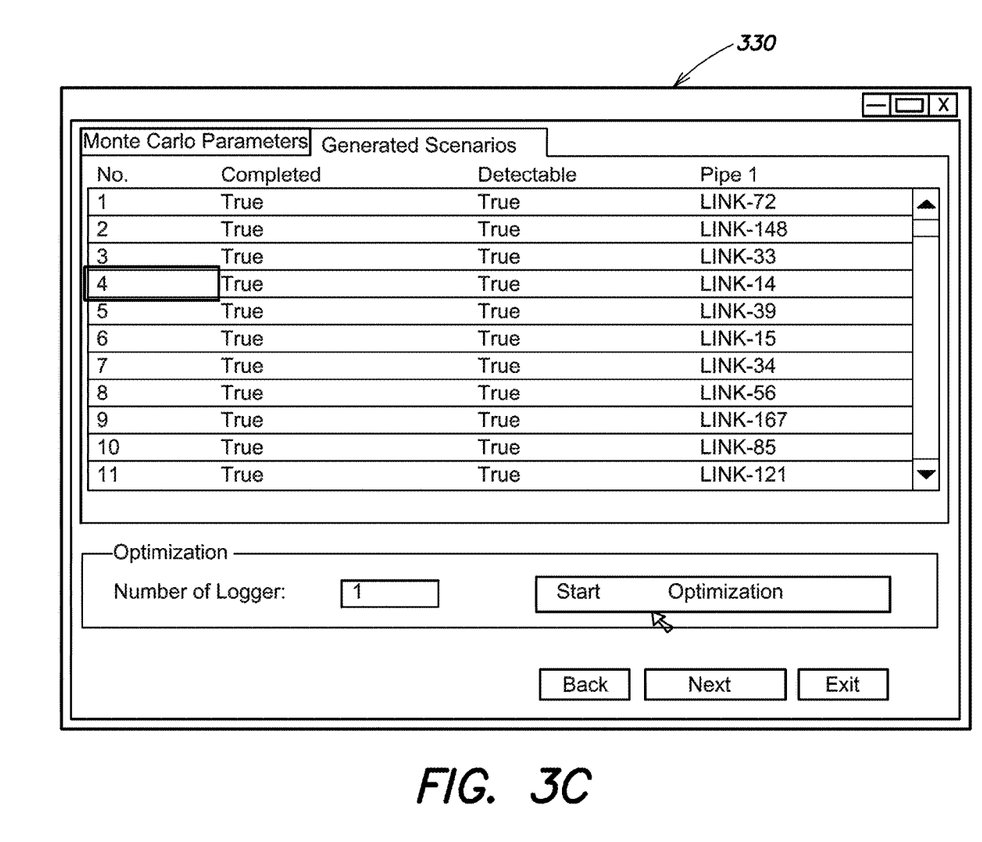
FIG. 3C is an example screen shot of a summary of simulation results UI screen.

At step 220, the scenario generation module 142 may utilize a Monte Carlo simulation algorithm to generate random target scenarios by randomly selecting pipe indexes identifying pipes, and randomly selecting pipe wall reaction coefficients within a valid range for those pipes. The number of simulations and minimum and a maximum number of pipes affected in each target scenario may be specified. The UI module 148 may present to a scenario generation UI screen that allows a user to make perform such tasks. FIG. 3B is a screen shot of an example scenario generation UI screen 320. At step 230, the simulation module 144 may simulate the target scenarios using the water quality model. A summary of simulation results UI screen may be displayed to the user by the UI module 148. FIG. 3C is an example screen shot of a summary of simulation results UI screen 330.

At step 240, the scenario generation module 142 may compare each of the target scenarios with a base scenario to determine if water quality is detectable at possible sensor locations. The comparison may involve comparing water quality at each of the is possible sensor locations for the target scenario (as determined by the simulation) and the base scenario. Water quality may be considered detectable when a difference between the target scenario and the base scenario is greater than a threshold (e.g., the accuracy of the water quality sensor). At step 250, the results from step 240 may be stored in the impact database 134. The results may be formatted as a binary matrix, where each binary value indicates whether water quality variation is detectable at a possible sensor location (e.g. 0 indicating not-detectable and 1 indicating detectable).

Figure 4:
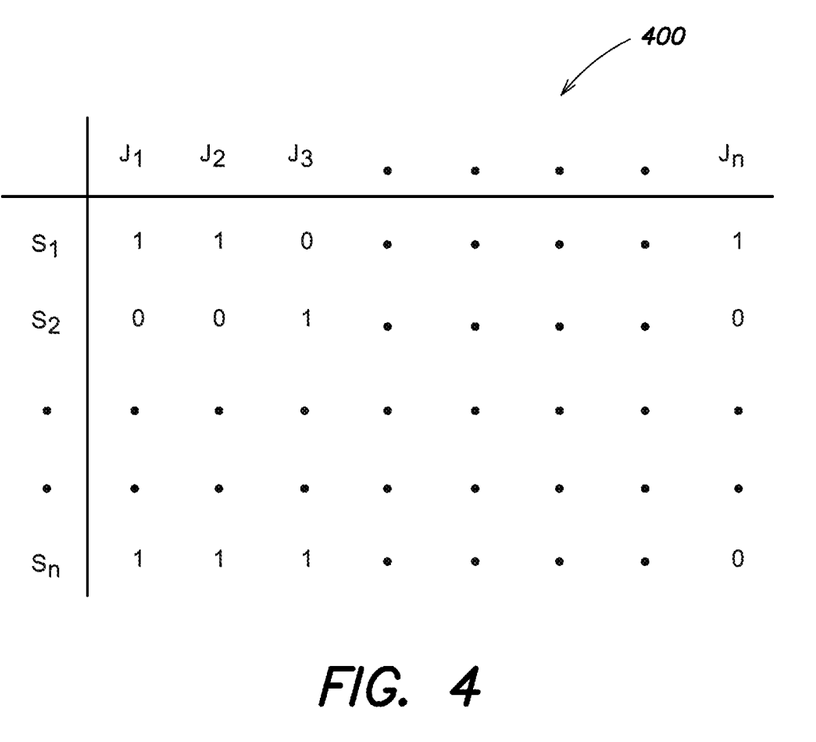
FIG. 4 is an example binary matrix which may be maintained by an impact database.

FIG. 4 is an example binary matrix 400 which may be maintained by the impact database 134. Each column may indicate a possible sensor location, in this example, a junction identified by an index $J_1$, $J_2$, $J_3$, etc. Each row may indicate a target scenario identified by an index $S_1$, $S_2$, $S_3$, etc. Since the matrix is built using only binary numbers, it may be very efficiently stored in memory 130, and require little processing power to access its members, regardless of its size (which depends on the number of possible sensor locations and the number of target scenarios).

Figure 3D:
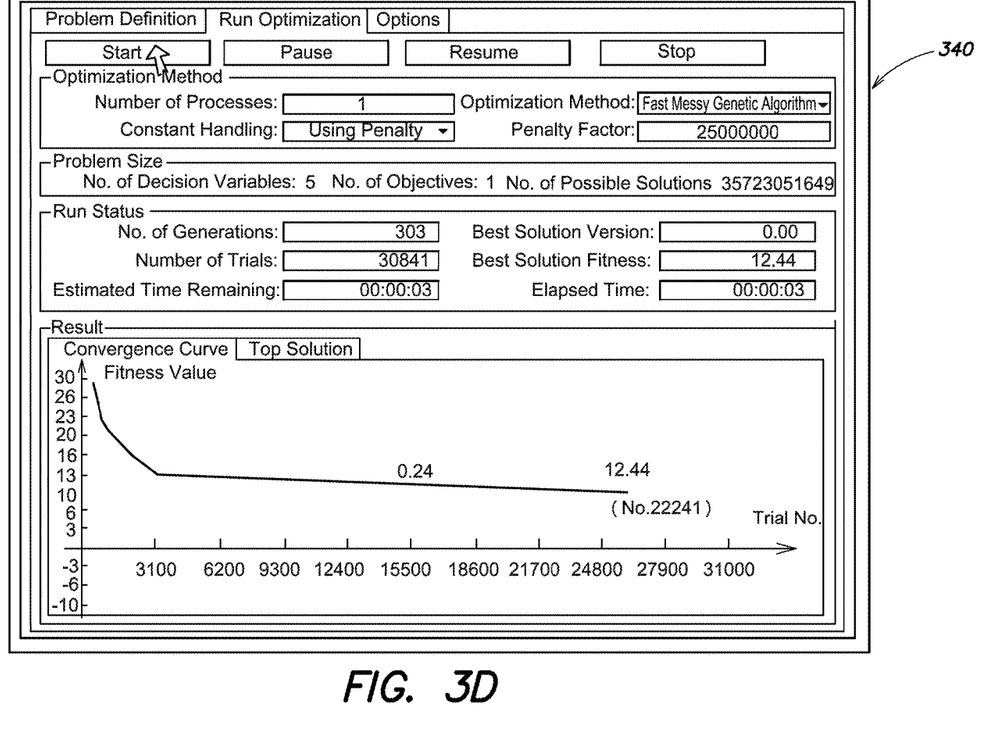
FIG. 3D is a screen shot of an example optimization results UI screen.

Returning to FIG. 2, and turning to the optimization of placement of a number of water quality sensors phase, at step 260 the optimization module 146 may generate a candidate water quality sensor location set including randomly generated sensor locations for the number of water quality sensors. At step 270, the optimization module 146 may calculate water quality sensor network efficiency for the candidate water quality sensor location set using equation (2) above and the information in the impact database 134. At step 280, stopping criteria may be checked. The stopping criteria may be a predetermined water quality sensor network efficiency being reached, the elapse of a certain period of time, or some other indication that the current candidate water quality sensor location set is sufficient. If the stopping criteria has not been reached, execution proceeds to step 290, where the optimization module 146 uses a genetic algorithm to evolve the initial candidate water quality sensor location set to produce subsequent water quality sensor location sets, using the computed water quality sensor network efficiency as a fitness value. If the stopping criteria has been reached, execution proceeds to step 295, where the optimized sensor location set may be displayed to a user. An optimization is results UI screen that shows the optimized sensor location set may be displayed to the user by the UI module 148. FIG. 3D is a screen shot of an example optimization results UI screen 340. Using the displayed optimized sensor location set, the user may then arrange for workers to apply water quality sensors at the locations there indicated.

In general, the analysis application 140 may be used with a wide variety of different types of water distribution networks, with varying numbers of pipes and water quality sensors. As the number of water quality sensors increases, the attainable sensor network efficiency will generally increase. However, if placed at near optimal locations, typically even a small number of water quality sensors (e.g., <15) may provide significant coverage. Such typical properties may be illustrated by example results of an example implementation.

Figure 5A:
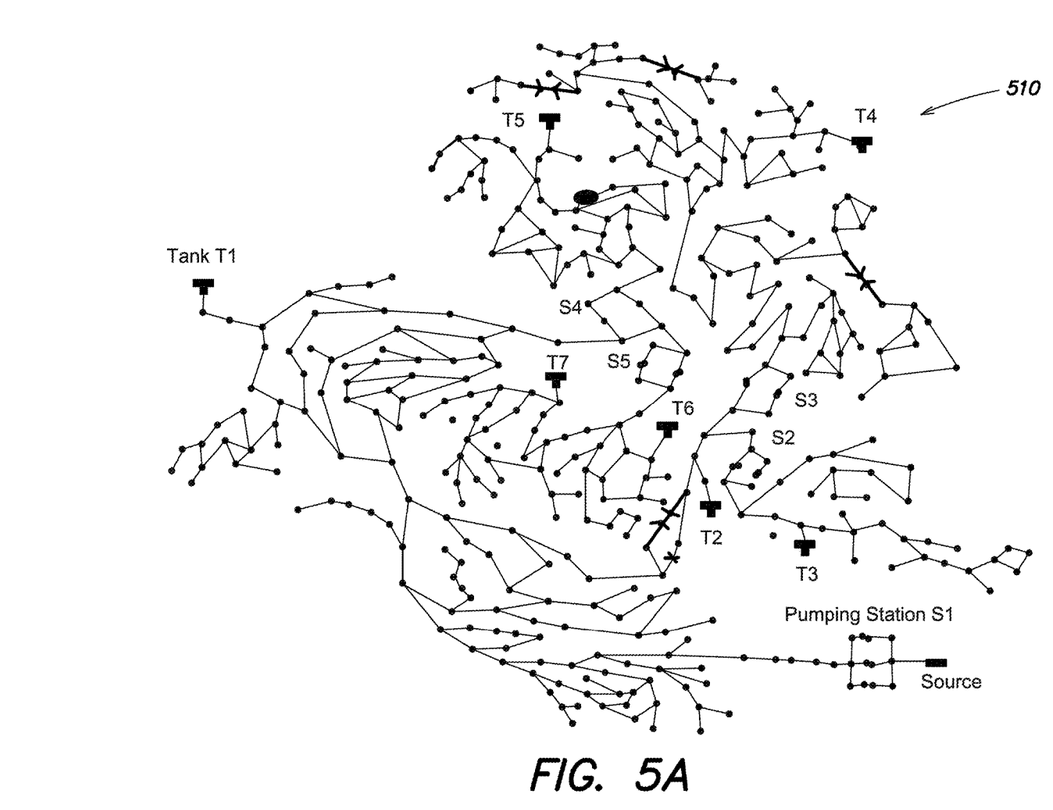
FIG. 5A is a diagram of the Battle of the Water Calibration Networks (BWCN) C-Town network, a well-known test network in research, showing one water quality sensor placed at a near optimal location.
Figure 5B:
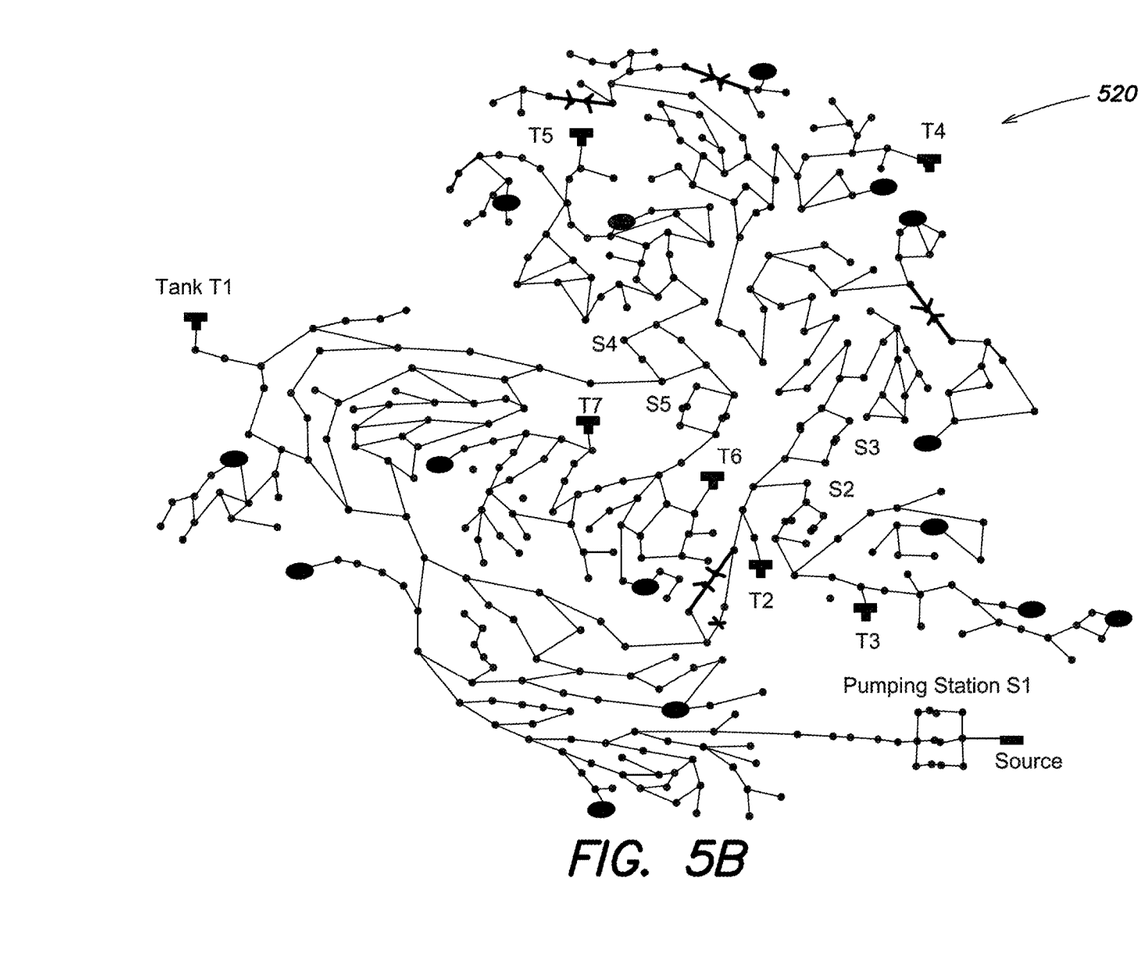
FIG. 5B is a diagram of the BWCN C-Town network showing fifteen water quality sensors placed at near optimal locations.
Figure 5C:
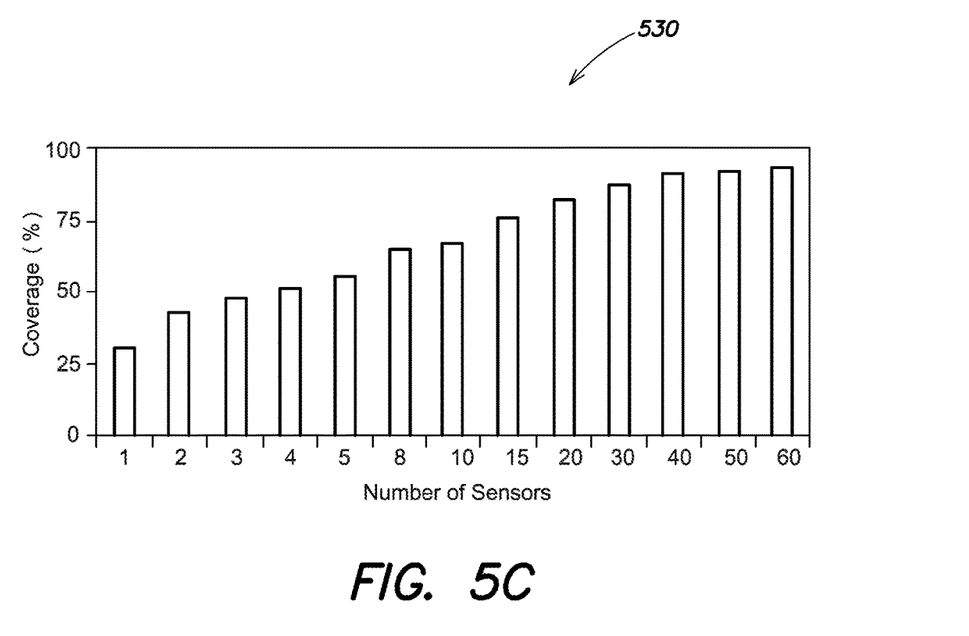
FIG. 5C is a graph showing a relationship between the number of water quality sensors placed at near optimal locations and coverage of the BWCN C-Town network.

FIG. 5A is a diagram 510 of the Battle of the Water Calibration Networks (BWCN) C-Town network, a well-known test network in research, showing one water quality sensor placed at a near optimal location determined using the above described techniques. FIG. 5B is a diagram 520 of the BWCN C-Town network showing fifteen water quality sensors placed at near optimal locations determined using the above described techniques. Further, FIG. 5C is a graph 530 showing a relationship between the number of water quality sensors placed at near optimal locations determined using the above described techniques and coverage of the BWCN C-Town network. As can be seen, the coverage in this test network shows only a very small amount of increase after the number of sensors reaches 15, when they are placed near optimally. In general, for a given system, more water quality sensors may not ensure significantly better coverage. A more cost effective approach generally is to place a limited number of water quality sensors optimally.

In summary, the above description details techniques for optimize water quality sensor placement by implementing a two-part optimization solution procedure, involving building an impact database, and determining an optimized water quality sensor location set using the impact database. It should be understood that various adaptations and modifications may be readily made to the techniques, to suit various implementations.

While the techniques are described above in reference to a water distribution network, it should be understood that the techniques may be applicable to other types of fluid delivery networks. Likewise the techniques may be adapted for use with various fluid collection systems.

In general, it should be understood that the techniques may be implemented in software, in hardware, or in a combination thereof. A software implementation may include electronic device-executable instructions stored in a non-transitory electronic device-readable medium, such as a volatile or persistent memory, a hard-disk, a compact disk (CD), or other storage medium. A hardware implementation may include specially configured processors, application specific integrated circuits (ASICs), and/or other types of hardware components. Further, a combined software/hardware implementation may include both electronic device-executable instructions stored in a non-transitory electronic device-readable medium, as well as one or more specially configured hardware components. Above all, it should be understood that the above descriptions are meant to be taken only by way of example.

What is claimed is:

1. A method of optimizing water quality sensor placement in a water distribution network, comprising:
   building, by an analysis application executing on an electronic device, an impact database that is stored on a non-transitory electronic device readable medium by:
   generating a plurality of target scenarios, and
   analyzing each target scenario to determine whether water quality variation is detectable at each of a plurality of possible sensor locations, wherein water quality is considered to be detectable at a sensor location when a change in pipe wall reaction coefficients leads to a change in water quality at the sensor location that is greater than a threshold;
   optimizing, by the analysis application executing on the electronic device, placement of a number of water quality sensors at the possible sensor locations by:
   generating a candidate water quality sensor location set by an optimization module of the analysis application,
   calculating water quality sensor network efficiency for the candidate water quality sensor location set using the impact database, wherein water quality sensor network efficiency is based on a length of pipes where water quality variations are detectable by at least one water quality sensor, and
   using, by the optimization module, the water quality sensor network efficiency to generate subsequent water quality sensor location sets that have greater water quality sensor efficiency until an optimized sensor location set that maximizes the length of pipes where water quality variations are detectable is produced; and
   applying water quality sensors at locations in the water distribution network indicated by the optimized sensor location set that maximize the length of pipes where water quality variations are detectable.

2. The method of claim 1, wherein the generating the plurality of target scenarios is performed using a Monte Carlo simulation algorithm that produces random target scenarios, and each random target scenario involves randomly selected values of pipe wall reaction coefficients for randomly selected pipes of the water distribution system.

3. The method of claim 1, wherein the analyzing each target scenario comprises:
   simulating the target scenario using a model of the water distribution system;
   comparing water quality at each the plurality of possible sensor locations with water quality at the respective possible sensor location in a base scenario; and
   determining water quality is detectable at a possible sensor location when a difference between water quality at the possible sensor location in the target scenario and water quality at the possible sensor location in the base scenario is greater than a threshold value.

4. The method of claim 1, wherein the impact database stores a binary matrix where each binary value indicates whether water quality variation is detectable at a corresponding possible sensor location in a corresponding target scenario.

5. The method of claim 1, wherein the optimization module utilizes a genetic algorithm, the candidate water quality sensor location set comprises randomly generated sensor locations for the number of water quality sensors, and the using the water quality sensor network efficiency to generate subsequent water quality sensor location sets comprises using the water quality sensor network efficiency as a fitness value in the genetic algorithm.

6. The method of claim 1, wherein the calculating water quality sensor network efficiency and using the water quality sensor network efficiency to generate subsequent water quality sensor location sets is performed iteratively until a stopping criteria is satisfied.

7. The method of claim 1, wherein the possible sensor locations coincide with junctions in the water distribution system.

8. The method of claim 1, wherein water quality is evaluated as a concentration of one or more chemical additives applied during water treatment.

9. The method of claim 1, further comprising:
receiving a user's selection of the number of water quality sensors.

10. A system comprising:
an electronic device having:
a display screen,
one or more processors configured to execute instructions, and
a memory configured to store an impact database describing a plurality of target scenarios involving the water distribution network, and instructions for a plurality of software modules of an analysis application that are executable on the one or more processors, the plurality of software modules including:
a scenario generation module configured to generate a plurality of target scenarios,
a simulation module configured to simulate each target scenario to determine whether water quality variation is detectable at each of a plurality of possible sensor locations, wherein water quality is considered to be detectable at a sensor location when a change in pipe wall reaction coefficients leads to a change in water quality at the sensor location that is greater than a threshold, the simulation module further configured to store the determinations in an impact database, and
an optimization module configured to optimize placement of a number of sensors based on water quality sensor network efficiency, wherein water quality sensor network efficiency is based on a length of pipes where water quality variations are detectable by at least one water quality sensor calculated from the impact database and the optimization maximizes the length of pipes where water quality variations are detectable; and
a plurality of sensors applied at locations in the water distribution network indicated by an optimized sensor location set that maximize the length of pipes where water quality variations are detectable, the plurality of sensors configured to operate to monitor water quality.

11. A method of optimizing water quality sensor placement in a water distribution network, comprising:
determining, by an analysis application executing on an electronic device, whether water quality variation is detectable at each of a plurality of possible sensor locations in a water distribution network for each a plurality of target scenarios, wherein water quality is considered to be detectable at a sensor location when a change in pipe wall reaction coefficients leads to a change in water quality at the sensor location that is greater than a threshold, and
optimizing, by the analysis application, placement of a number of water quality sensors to produce an optimized water quality sensor location set by determining candidate water quality sensor location sets, calculating water quality sensor network efficiency for the candidate water quality sensor location sets using the determined water is quality variation detectability, and evolving the candidate water quality sensor location sets based on the calculated water quality sensor network efficiency until an optimized sensor location set is produced that maximizes the length of pipes where water quality variations are detectable; and
applying water quality sensors at locations in the water distribution network indicated by the optimized sensor location set that maximize the length of pipes where water quality variations are detectable.

12. The method of claim 11, further comprising:
building an impact database based on the determined water quality variation detectability at each of the plurality of possible sensor locations in the water distribution network for each the plurality of target scenarios.

13. The method of claim 12, wherein the building the impact database comprises:
using a Monte Carlo simulation algorithm to produce random target scenarios, wherein each random target scenario involves randomly selected values of pipe wall reaction coefficients for randomly selected pipes of the water distribution system.

14. The method of claim 11, wherein the building the impact database further comprises:
simulating target scenarios using a model of the water distribution system; and
for each target scenario,
comparing water quality at each the plurality of possible sensor locations with water quality at a respective possible sensor location in a base scenario, and
determining water quality is detectable at a possible sensor location when a difference between water quality at the possible sensor location in the target scenario and water quality at the possible sensor location in the base scenario is greater than a threshold value.

15. The method of claim 11, wherein the optimizing placement of the number of water quality sensors further comprises:
executing a genetic algorithm that uses random water quality sensor locations to produce the candidate water quality sensor location sets, and using the water quality sensor network efficiency as a fitness value to generate subsequent water quality sensor location sets, wherein a subsequent water quality sensor location set reached at a stopping criteria is returned as the optimized water quality sensor location set.

* * * * *

UNITED STATES PATENT AND TRADEMARK OFFICE
CERTIFICATE OF CORRECTION

PATENT NO. : 10,161,749 B1
APPLICATION NO. : 14/726189
DATED : December 25, 2018
INVENTOR(S) : Zheng Yi Wu et al.

It is certified that error appears in the above-identified patent and that said Letters Patent is hereby corrected as shown below:

In the Specification

Column 4, Line 33 reads:
"distribution is modeling and management solution available"
Should read:
--distribution modeling and management solution available--

Column 5, Line 15 reads:
"potential location, initial pipe wall reaction coefficients is"
Should read:
--potential location, initial pipe wall reaction coefficients--

Column 6, Line 2 reads:
"may operate to solve the is water quality sensor placement"
Should read:
--may operate to solve the water quality sensor placement--

Column 6, Line 41 reads:
"quality at each of the is possible sensor locations for the"
Should read:
--quality at each of the possible sensor locations for the--

Column 7, Line 17 reads:
"optimization is results UI screen that shows the optimized"
Should read:
--optimization results UI screen that shows the optimized--

Signed and Sealed this
Seventeenth Day of September, 2019

Andrei Iancu
*Director of the United States Patent and Trademark Office*

CERTIFICATE OF CORRECTION (continued)
U.S. Pat. No. 10,161,749 B1

In the Claims

Claim 11, Column 10, Line 18 reads:
"mined water is quality variation detectability, and"
Should read:
--mined water quality variation detectability, and--